United States Patent
Karicherla et al.

(10) Patent No.: US 7,908,017 B1
(45) Date of Patent: Mar. 15, 2011

(54) LEAD DEPLOYABLE MYOCARDIAL INFARCTION PATCH

(75) Inventors: Annapurna Karicherla, Valencia, CA (US); Kevin L. Morgan, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 1004 days.

(21) Appl. No.: 11/467,884

(22) Filed: Aug. 28, 2006

(51) Int. Cl.
*A61N 1/05* (2006.01)

(52) U.S. Cl. .......................... 607/129; 607/122; 607/126

(58) Field of Classification Search ................ 600/3, 16, 600/37, 372, 374; 623/23.64, 2.36; 607/115–130, 607/2, 3, 36, 37, 45, 9; 128/898, 785, 419 P; 604/501–510
See application file for complete search history.

(56) References Cited

U.S. PATENT DOCUMENTS

| | | | | |
|---|---|---|---|---|
| 5,249,574 A | * | 10/1993 | Bush et al. | 607/9 |
| 5,370,650 A | * | 12/1994 | Tovey et al. | 606/151 |
| 7,319,905 B1 | * | 1/2008 | Morgan et al. | 607/129 |
| 2002/0019623 A1 | * | 2/2002 | Altman et al. | 604/508 |
| 2002/0169359 A1 | | 11/2002 | McCarthy et al. | |
| 2002/0188170 A1 | | 12/2002 | Santamore et al. | |
| 2003/0078671 A1 | | 4/2003 | Lesniak et al. | |
| 2004/0010180 A1 | * | 1/2004 | Scorvo | 600/16 |
| 2004/0133063 A1 | | 7/2004 | McCarthy et al. | |
| 2004/0267083 A1 | | 12/2004 | McCarthy et al. | |
| 2005/0080402 A1 | | 4/2005 | Santamore et al. | |

FOREIGN PATENT DOCUMENTS

| | | |
|---|---|---|
| WO | 0224159 A2 | 3/2002 |
| WO | 0224159 A3 | 3/2002 |
| WO | 02087481 A1 | 11/2002 |
| WO | 03090716 A1 | 11/2003 |

* cited by examiner

*Primary Examiner* — Carl H Layno
*Assistant Examiner* — Paula J Stice (57) ABSTRACT

A method of delivering a myocardial infarction patch to a surface of a heart is disclosed herein. In one embodiment, the method includes deploying the patch from an intra pericardial lead.

20 Claims, 10 Drawing Sheets

LEAD DEPLOYABLE MYOCARDIAL INFARCTION PATCH

FIELD OF THE INVENTION

The present invention relates to medical apparatus and methods. More specifically, the present invention relates to myocardial infarction patches and methods of deploying such patches.

BACKGROUND OF THE INVENTION

A myocardial infarction is the irreversible damage done to a segment of heart muscle by ischemia, where the myocardium is deprived of adequate oxygen and metabolite removal due to an interruption in blood supply. Ischemia is usually due to a sudden thrombotic occluion of a coronary artery, commonly called a heart attack.

If the coronary artery becomes completely occluded and there is poor collateral blood flow to the affected area, a transmural or full-wall thickness infarct can result in which much of the contractile function of the area is lost. Over a period of one to two months, the necrotic tissue heals, leaving a scar. The most extreme example of this is a ventricular aneurysm where all of the muscle fibers in the area are destroyed and replaced by fibrous scar tissue.

Even if the ventricular dysfunction as a result of the infarct is not immediately life-threatening, a common sequela of a transmural myocardial infarction in the left ventricle is heart failure brought about by ventricular remodeling. Heart failure refers to a condition where cardiac output falls below a level adequate to meet the metabolic needs of the body which, if uncompensated, leads to rapid death.

It is believed that preventing heart remodeling can prevent heart failure. Placing patches or substrates over the myocardial infarction is a therapy used to prevent heart remodeling. Such patches or substrates are implanted via highly invasive open chest procedures.

There is a need in the art for a patch or substrate that is deliverable to a myocardial infarction via less invasive methods. There is also a need for a less invasive method of delivering a patch or substrate to a myocardial infarction.

SUMMARY

A method of delivering a myocardial infarction patch to a surface of a heart is disclosed herein. In one embodiment, the method includes deploying the patch from an intra pericardial lead.

A pericardial lead is disclosed herein. In one embodiment, the pericardial lead includes a myocardial patch.

A myocardial patch is disclosed herein. In one embodiment, the myocardial patch is adapted to be delivered to a heart surface via a pericardial lead having a lumen. The patch includes a framework and a mesh. The framework includes a lumen. The mesh extends between portions of the framework. When the patch is being delivered via the lead, the lead lumen extends into the framework lumen.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

The present application describes myocardial infarction patches 10 that are deployable via a pericardial lead 15. In some embodiments, the patch 10 is an integral part of a lead 15. In other embodiments, the patch 10 is a separate assembly that is carried on a lead 15.

The present application also describes methods of delivering such patches 10 to a myocardial infarction site on the exterior surface of a heart. The patches 10 and delivery methods are advantageous in that they facilitate non-invasive deployment of myocardial infarction patches 10.

Figure 1:
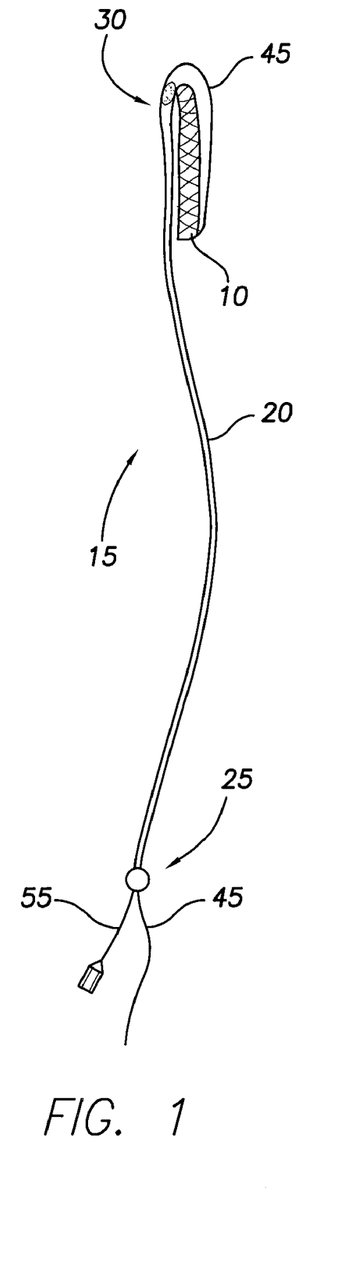
FIG. 1 is an overall view of the patch and lead, wherein the patch is in a non-deployed or unexpanded state.
Figure 2:
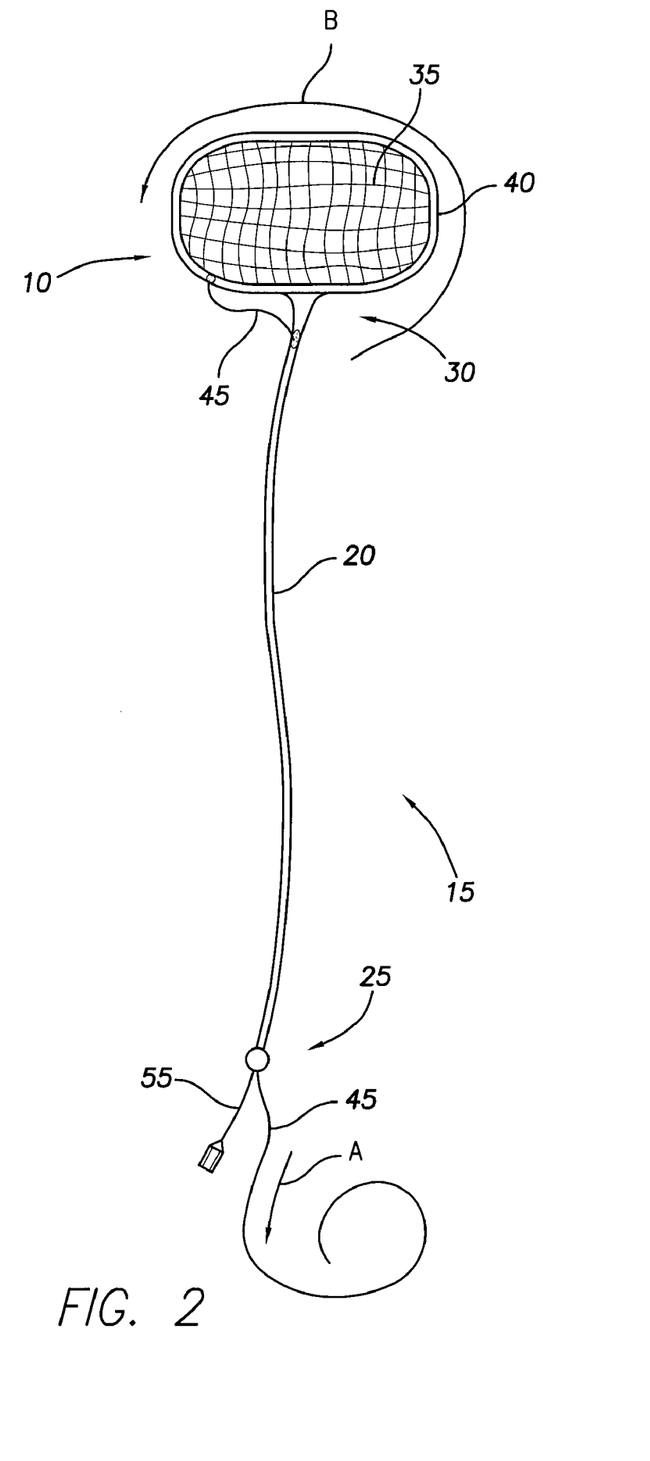
FIG. 2 is the same view as FIG. 1, except the patch is in a deployed or expanded state.
Figure 3:
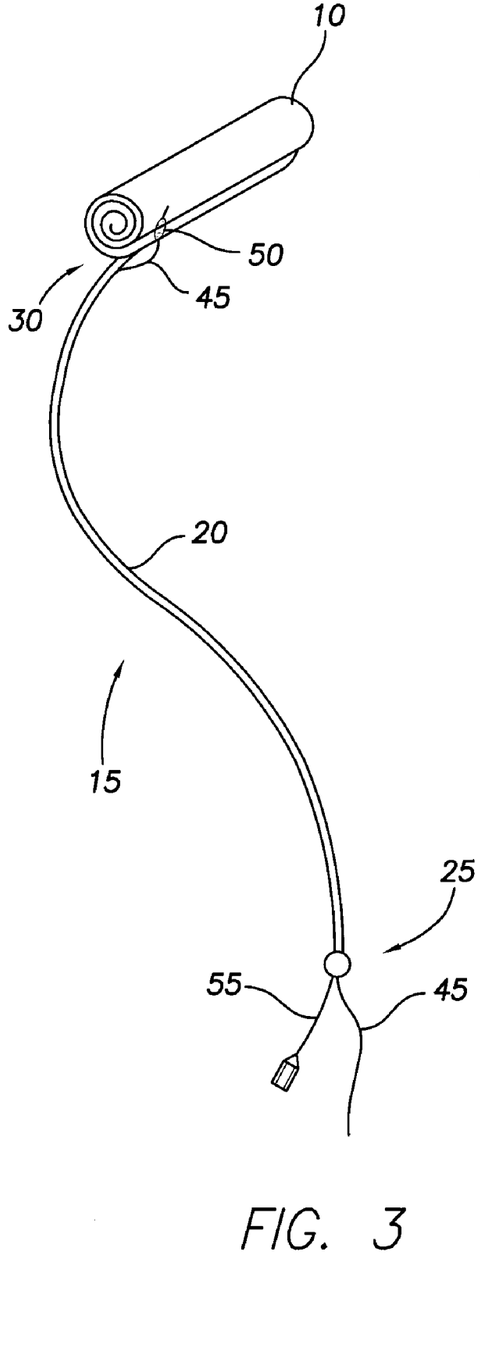
FIG. 3 is an overall view of the patch and lead, wherein the patch is in a non-deployed or unexpanded state.
Figure 4:
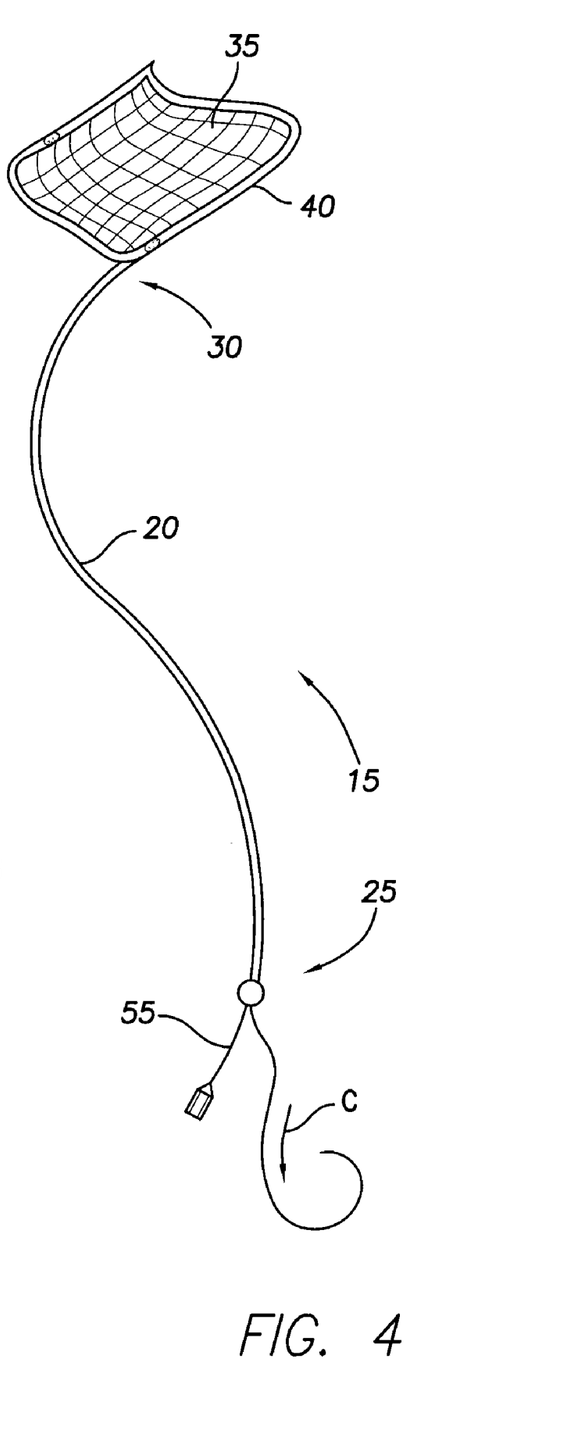
FIG. 4 is the same view as FIG. 3, except the patch is in a deployed or expanded state.
Figure 5:
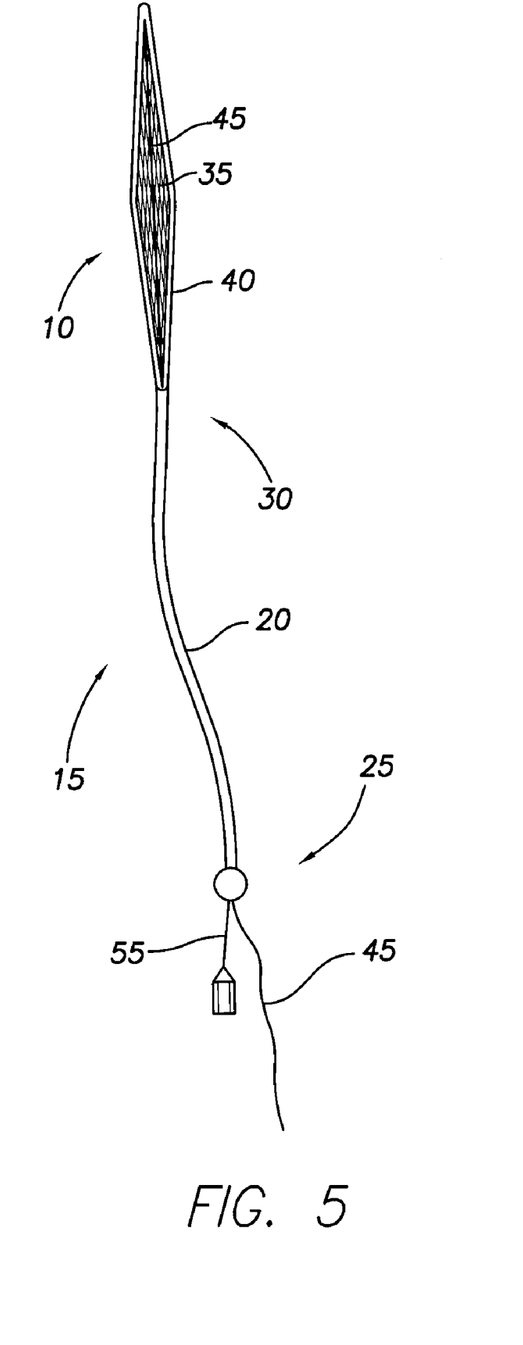
FIG. 5 is an overall view of the patch and lead, wherein the patch is in a non-deployed or unexpanded state.
Figure 6:
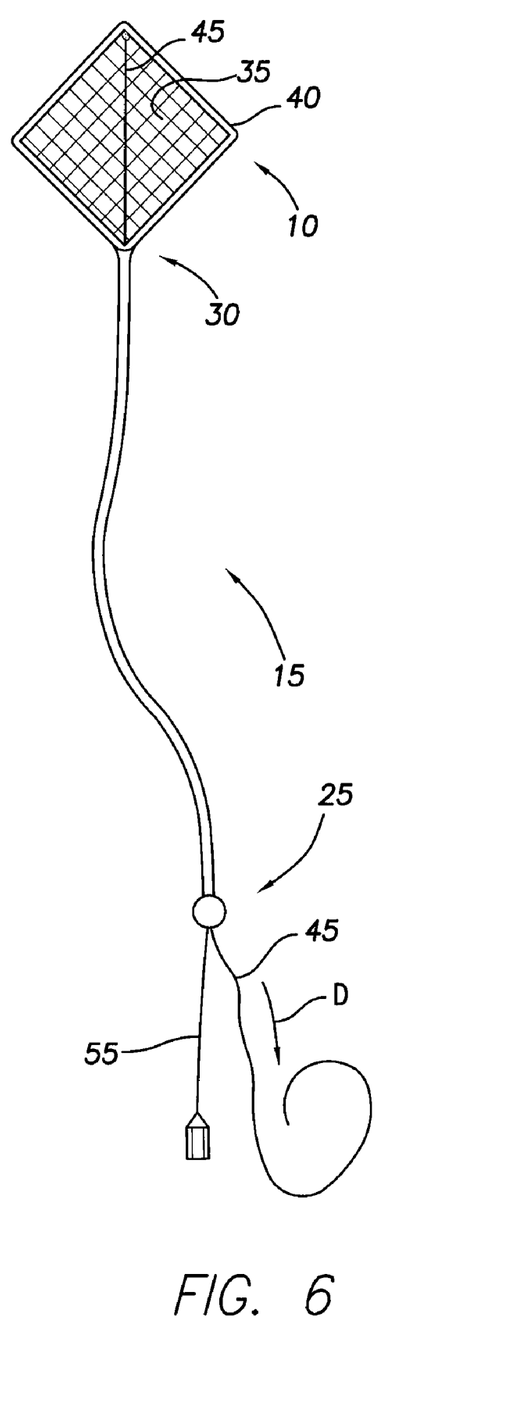
FIG. 6 is the same view as FIG. 5, except the patch is in a deployed or expanded state.

For a detailed discussion of various embodiments of the patch 10, associated lead 15 and method of deploying the patch 10, reference is made to FIGS. 1-6. FIGS. 1, 3 and 5 are overall views of different embodiments of the patch 10 and lead 15, wherein the patches 10 are in non-deployed or unexpanded states. FIGS. 2, 4 and 6 are the same views as FIGS. 1, 3 and 5, except the patches 10 are in deployed or expanded states.

As shown in FIGS. 2, 4 and 6, in various embodiments, each lead 15 includes an elongated tubular body 20 having proximal and distal ends 25, 30. In one embodiment, each patch 10 is located on the distal end 30 of the lead body 20 and includes a mesh 35 (e.g., a mesh, weave, fabric, etc.) and a boarder or framework 40. In other embodiments, each patch 10 is located on more proximal portions of the lead body 20.

As depicted in FIGS. 2, 4 and 6, each mesh 35 is attached to the framework 40, which defines an area across which the mesh 35 extends when the patch 30 is in the deployed state. In one embodiment, the mesh 35 is made of metal materials (Nitinol, stainless steel, etc.) or polymer materials (e.g., DACRON®, polyesters, electroactive polymers, conducting polymers, silicones, polyurethanes, etc., or any combination thereof). In one embodiment, the framework 40 or framework tubing is made of Nitinol, polytetrafluoroethylene ("PTFE"), silicone, polyurethane, etc., or the same material forming the lead body 20.

In some embodiments, as shown in FIGS. 2 and 6, the framework 40 is separate from the lead body 20 and is releasably or permanently attached to the distal end 30 of the lead body 20. In other embodiments, as depicted in FIG. 4, the distal end 30 of the lead body 20 forms the framework 40 by the distal end 30 coming about on itself to define the area across which the mesh 35 extends when in the patch 10 is in the deployed state. In other embodiments, as described later in this Detailed Description, the distal end 30 of the lead body 20 forms the framework 40 by the distal end splitting into branches, or otherwise defining the area across which the mesh 35 extends when the patch 10 is in the deployed state.

As illustrated in FIGS. 1 and 3, in various embodiments, when the patch 10 is in the non-deployed or unexpanded state, the patch 10 is folded, rolled or furled about itself along side the distal end 30 or a more proximal portion of the lead body 20. In other embodiments, when the patch 10 is in the non-deployed or unexpanded state, the patch 10 is folded, rolled or furled about the distal end 30 or a more proximal portion of the lead body 20. As depicted in FIG. 5, in various embodiments, when the patch 10 is in the non-deployed or unexpanded state, the patch 10 is folded, rolled or furled about itself at the distal end 30 or a more proximal portion of the lead body 20.

As shown in FIG. 1, in one embodiment, a drawstring 45 extends from a distal end of the unexpanded patch 10, over the distal end 30 of the lead body 20 and the proximal end of the patch 10, through the lead body 20 and out the proximal end 25 of the lead body 20. In one embodiment, the drawstring 45 attaches to the framework 40. In another embodiment, the drawstring 45 is attached to the mesh 35 by being interwoven into the mesh 35 or otherwise connected to the mesh 35 (e.g., via an adhesive).

As depicted in FIG. 2, the patch 10 is deployed into the expanded or deployed state by pulling on the proximal end of the drawstring 45 (as indicated in by arrow A). As a result, the patch 10 pivots from about or along the distal end 30 of the lead body 20 and unfolds, unrolls or unfurls into the deployed state (as indicated by arrow B).

As shown in FIG. 3, in one embodiment, the patch 10 is biased to deploy into the expanded state and includes an anchoring mechanism 50 (e.g., a pull-pin, latch, clip, barb, suture, etc.) that maintains the patch 10 is a non-expanded state. A drawstring 45 extends from an anchoring mechanism 50, through the lead body 20 and out the proximal end 25 of the lead body 20.

As depicted in FIG. 4, the patch 10 is deployed into the expanded or deployed state by pulling on the proximal end of the drawstring 45 (as indicated in by arrow C). As a result, the anchoring mechanism 50 is caused to release, which allows the patch 10 to unfold, unroll or unfurl into the deployed state.

As shown in FIG. 5, in one embodiment, when the patch 10 is in the non-deployed state, the patch 10 is shaped as a collapsed parallelogram with a width that is less than the internal diameter of an introducer used to deliver the lead 15 and patch 10 to the heart. A drawstring 45 extends from a distal end of the unexpanded patch 10, through the lead body 20 and out the proximal end 25 of the lead body 20. In one embodiment, the drawstring 45 attaches to the framework 40. In another embodiment, the drawstring 45 is attached to the mesh 35 by being interwoven into the mesh 35 or otherwise connected to the mesh 35 (e.g., via an adhesive).

As depicted in FIG. 6, the patch 10 is deployed into the expanded or deployed state by pulling on the proximal end of the drawstring 45 (as indicated in by arrow D). As a result, the patch 10 is caused to expand from the collapsed parallelogram of the non-deployed state to a square or rectangular shape of the deployed state.

To implant the patch 10, a lead 15 with a non-expanded patch 10 (see FIGS. 1, 3 and 5) located thereon is loaded distal end first into an introducer sheath. The lead 15, with the patch 10 located thereon, is advanced to the exterior surface of the heart via the introducer sheath. The introducer sheath is withdrawn sufficiently to place the non-expanded patch 10 adjacent a myocardial infarction. Once properly positioned relative to the myocardial infarction, the patch 10 is deployed into the expanded state depicted in FIGS. 2, 4 and 6. Both prior to and after deployment, the patch can be positioned via a stylet or guidewire 55 extending through the tubular lead body 20 to the patch 10.

Figure 7:
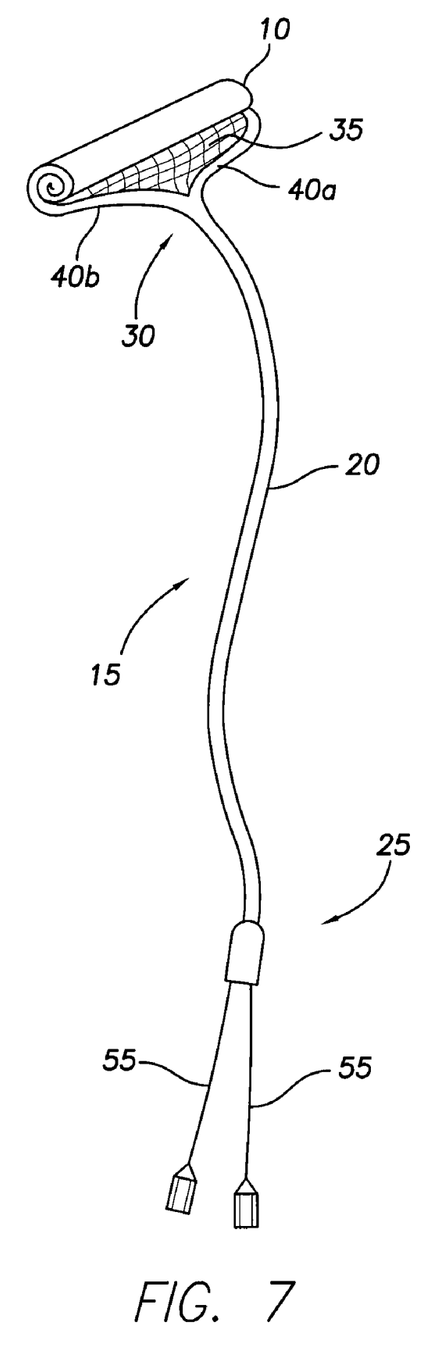
FIG. 7 is an overall view of the patch and lead, wherein the patch is in a non-deployed or unexpanded state.
Figure 8:
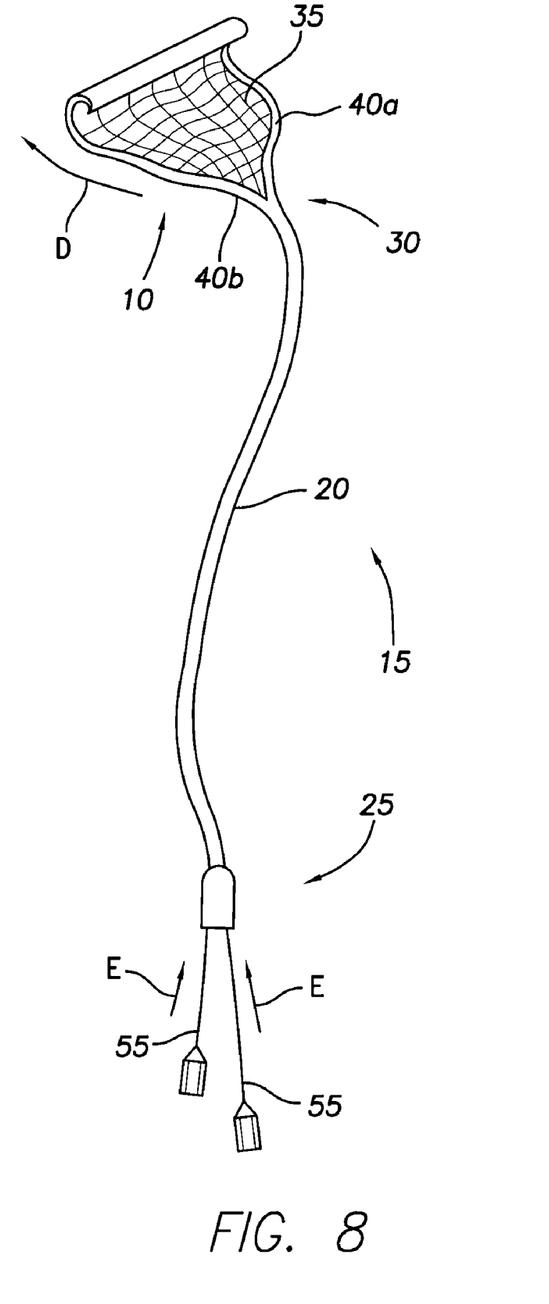
FIG. 8 is the same view as FIG. 7, except the patch is in a deployed or expanded state.
Figure 9:
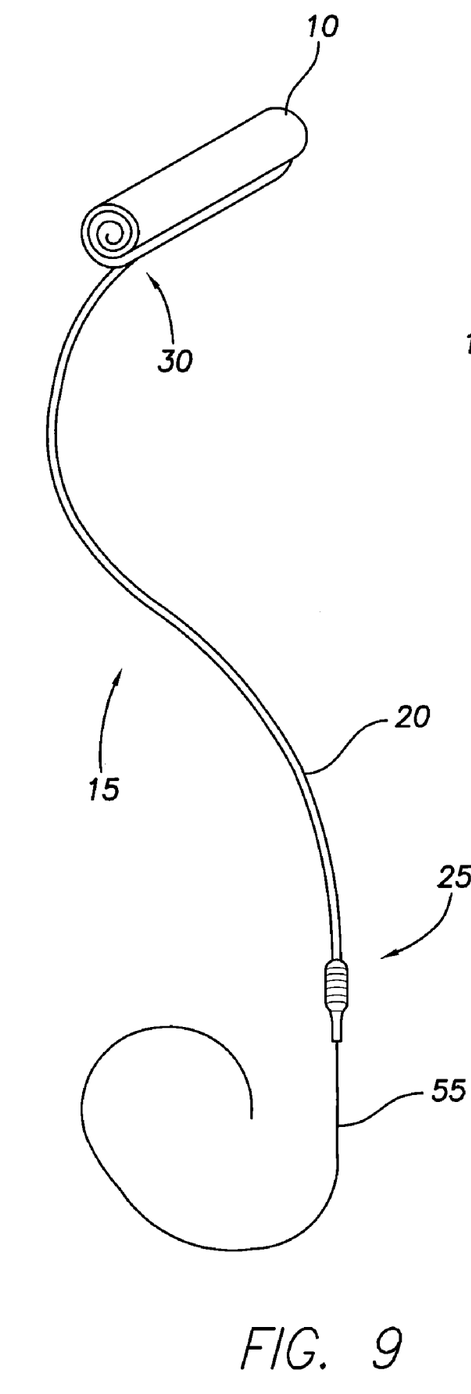
FIG. 9 is an overall view of the patch and lead, wherein the patch is in a non-deployed or unexpanded state.
Figure 10:
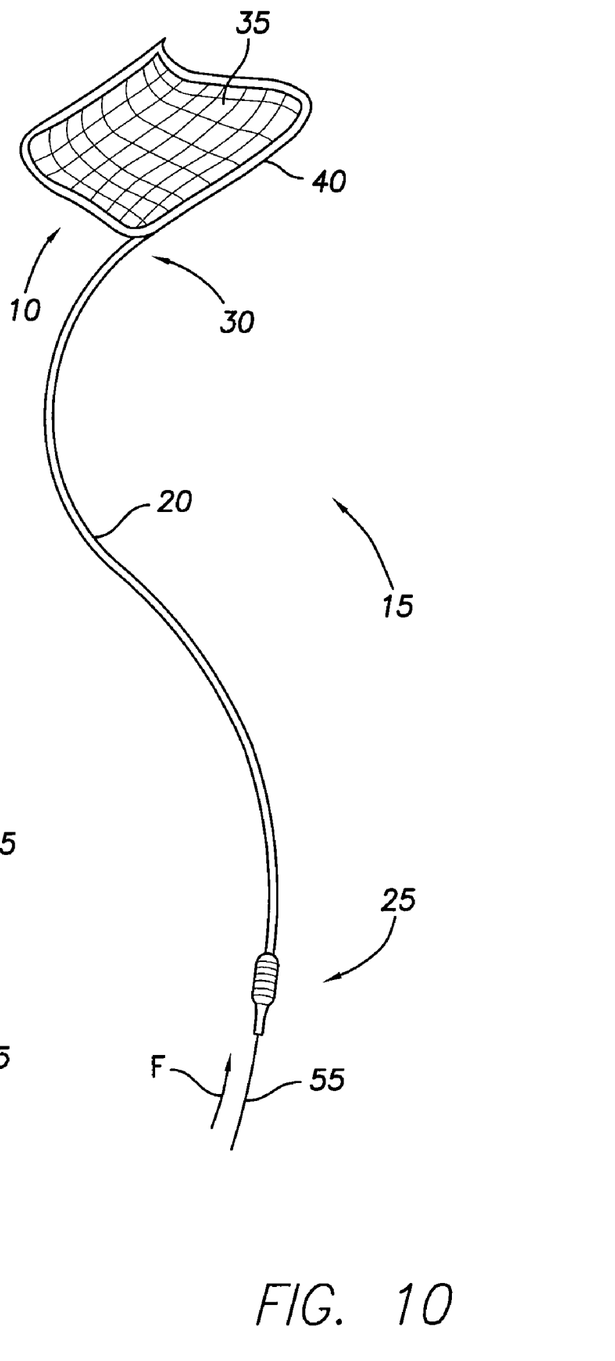
FIG. 10 is the same view as FIG. 9, except the patch is in a deployed or expanded state.

For a detailed discussion of other embodiments of the patch 10, associated lead 15 and method of deploying the patch 10, reference is made to FIGS. 7-10. FIGS. 7 and 9 are overall views of different embodiments of the patch 10 and lead 15, wherein the patches 10 are in non-deployed or unexpanded states. FIGS. 8 and 10 are the same views as FIGS. 7 and 9, except the patches 10 are in deployed or expanded states.

As shown in FIGS. 8 and 10, in various embodiments, each lead 15 includes an elongated tubular body 20 having proximal and distal ends 25, 30. In one embodiment, each patch 10 is located on the distal end 30 of the lead body 20 and includes a mesh 35 (e.g., a mesh, weave, fabric, etc.) and a boarder or framework 40. In other embodiments, each patch 10 is located on more proximal portions of the lead body 20.

As depicted in FIGS. 8 and 10, each mesh 35 is attached to the framework 40, which defines an area across which the mesh 35 extends when the patch 30 is in the deployed state. In one embodiment, the mesh 35 is made of metal materials (Nitinol, stainless steel, etc.) or polymer materials (e.g., DACRON®, polyesters, electroactive polymers, conducting polymers, silicones, polyurethanes, etc., or any combination thereof). In one embodiment, the framework 40 or framework tubing is made of Nitinol, PTFE, silicone, polyurethane, etc., or the same material forming the lead body 20.

In some embodiments, as depicted in FIG. 8, the distal end 30 of the lead body 20 forms the framework 40 by the distal end splitting into branches 40a, 40b to define the area across which the mesh 35 extends when in the patch 10 is in the deployed state. In other embodiments, as shown in FIG. 10, the distal end 30 of the lead body 20 forms the framework 40 by the distal end 30 coming about on itself to define the area across which the mesh 35 extends when in the patch 10 is in the deployed state. In other embodiments, the lead body 20 is otherwise configured to define the area across which the mesh 35 extends when the patch 10 is in the deployed state. In other embodiments, the framework 40 is separate from the lead body 20 and is releasably or permanently attached to the distal end 30 of the lead body 20. With respect to the embodiments depicted in FIGS. 7-10, regardless of whether the framework 40a, 40b is formed from a separate tubular body or is some extension of the lead tubular body 20, the framework 40a, 40b has a lumen that communicates with the lumen of the lead tubular body 20, thereby allowing a stylet or guidewire 55 to extend from the lead body 20 and into the framework 40, 40a, 40b.

As illustrated in FIG. 9, in various embodiments, when the patch 10 is in the non-deployed or unexpanded state, the patch 10 is folded, rolled or furled about itself along side the distal end 30 or a more proximal portion of the lead body 20. In other embodiments, when the patch 10 is in the non-deployed or unexpanded state, the patch 10 is folded, rolled or furled about the distal end 30 or a more proximal portion of the lead body 20. As depicted in FIG. 7, in various embodiments, when the patch 10 is in the non-deployed or unexpanded state, the patch 10 is folded, rolled or furled about itself at the distal end 30 or a more proximal portion of the lead body 20.

As shown in FIG. 7, in one embodiment, one or more stylets or guidewires 55 are extended from the proximal end 25 of the lead tubular body 20, through the lead tubular body 20, and to the junction between the branches 40a, 40b. As depicted in FIG. 8, the patch 10 is deployed into the expanded or deployed state by extending a stylet or guidewire 55 distally into each branch 40a, 40b of the framework 40 (as indicated in by arrow E). As a result, the patch 10 unfolds, unrolls or unfurls into the deployed state.

As shown in FIG. 9, in one embodiment, a stylet or guidewire 55 is extended from the proximal end 25 of the lead tubular body 20, through the lead tubular body 20, and to the junction between the lead body 20 and the framework 40. As depicted in FIG. 10, the patch 10 is deployed into the expanded or deployed state by extending the stylet or guidewire 55 distally into the framework 40 (as indicated in by arrow F). As a result, the patch 10 unfolds, unrolls or unfurls into the deployed state.

To implant the patch 10, a lead 15 with a non-expanded patch 10 (see FIGS. 7 and 9) located thereon is loaded distal end first into an introducer sheath. The lead 15, with the patch 10 located thereon, is advanced to the exterior surface of the heart via the introducer sheath. The introducer sheath is withdrawn sufficiently to place the non-expanded patch 10 adjacent a myocardial infarction. Once properly positioned relative to the myocardial infarction, the patch 10 is deployed into the expanded state depicted in FIGS. 8 and 10. Both prior to and after deployment, the patch can be positioned via a stylet or guidewire 55 extending through the tubular lead body 20 to the patch 10.

For a detailed discussion of various embodiments of the patch 10, associated lead 15 and method of deploying the patch 10, reference is made to FIGS. 11-20. FIGS. 11, 13, 15, 17 and 19 are overall views of different embodiments of the patch 10 and lead 15, wherein the patches 10 are in non-deployed or unexpanded states. FIGS. 12, 14, 16, 18 and 20 are the same views as FIGS. 11, 13, 15, 17 and 19, except the patches 10 are in deployed or expanded states.

As shown in FIGS. 12, 14, 16, 18 and 20, in various embodiments, each lead 15 includes an elongated tubular body 20 having proximal and distal ends 25, 30. In one embodiment, each patch 10 is located on the distal end 30 of the lead body 20 and includes a mesh 35 (e.g., a mesh, weave, fabric, etc.) and a boarder or framework 40, 40a, 40b. In other embodiments, each patch 10 is located on more proximal portions of the lead body 20.

As depicted in FIGS. 12, 14, 16, 18 and 20, each mesh 35 is attached to the framework 40, which defines an area across which the mesh 35 extends when the patch 30 is in the deployed state. In one embodiment, the mesh 35 is made of metal materials (Nitinol, stainless steel, etc.) or polymer materials (e.g., DACRON®, polyesters, electroactive polymers, conducting polymers, silicones, polyurethanes, etc., or any combination thereof). In one embodiment, the framework 40 or framework tubing is made of Nitinol, PTFE, silicone, polyurethane, etc., or the same material forming the lead body 20.

Figure 12:
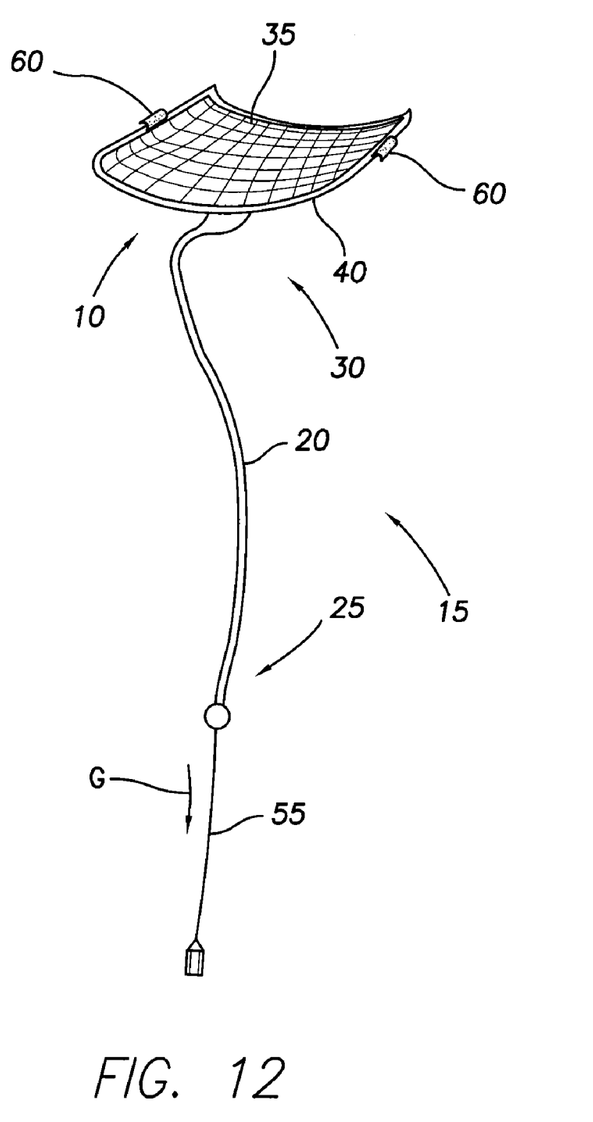
FIG. 12 is the same view as FIG. 11, except the patch is in a deployed or expanded state.
Figures 13, 14:
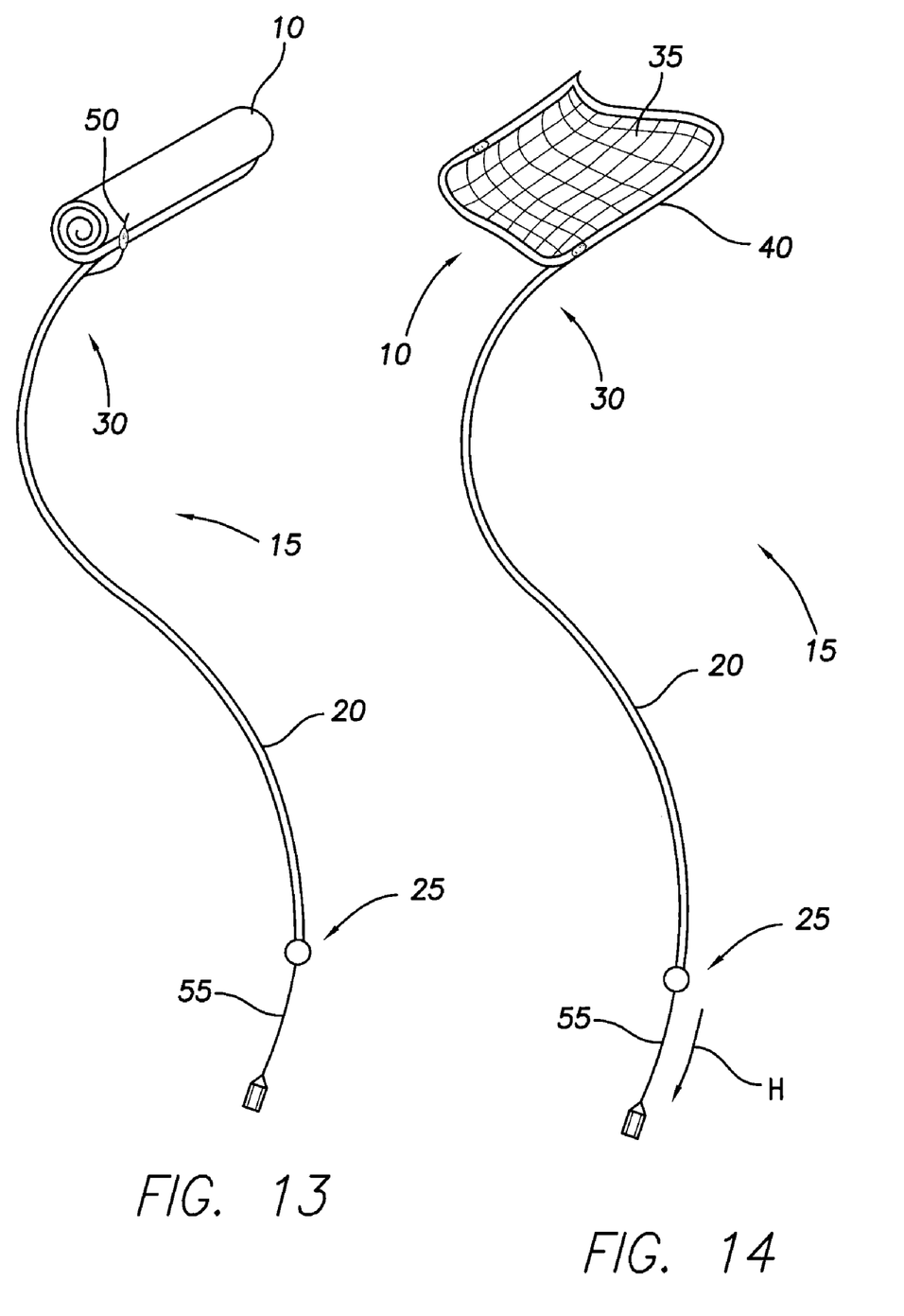
FIG. 13 is an overall view of the patch and lead, wherein the patch is in a non-deployed or unexpanded state.
FIG. 14 is the same view as FIG. 13, except the patch is in a deployed or expanded state.
Figures 15, 16:
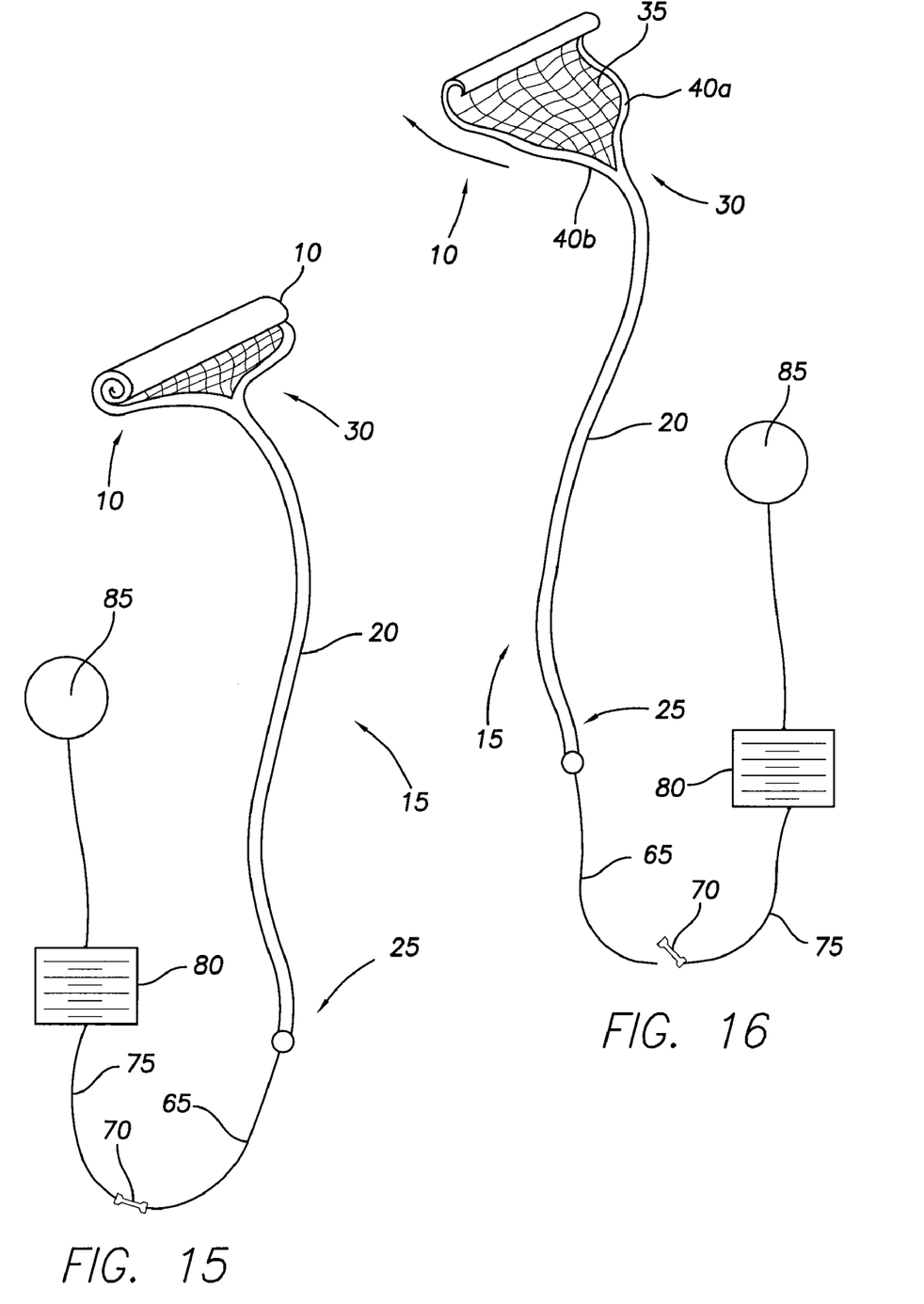
FIG. 15 is an overall view of the patch and lead, wherein the patch is in a non-deployed or unexpanded state.
FIG. 16 is the same view as FIG. 15, except the patch is in a deployed or expanded state.
Figure 18:
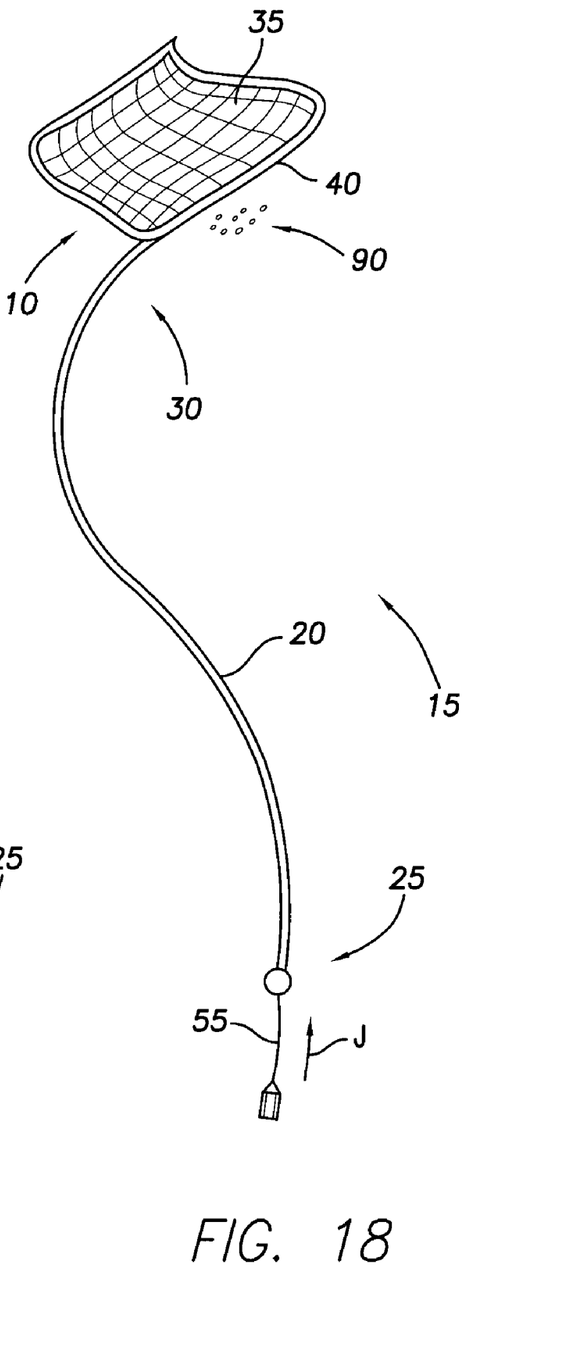
FIG. 18 is the same view as FIG. 17, except the patch is in a deployed or expanded state.
Figures 19, 20:
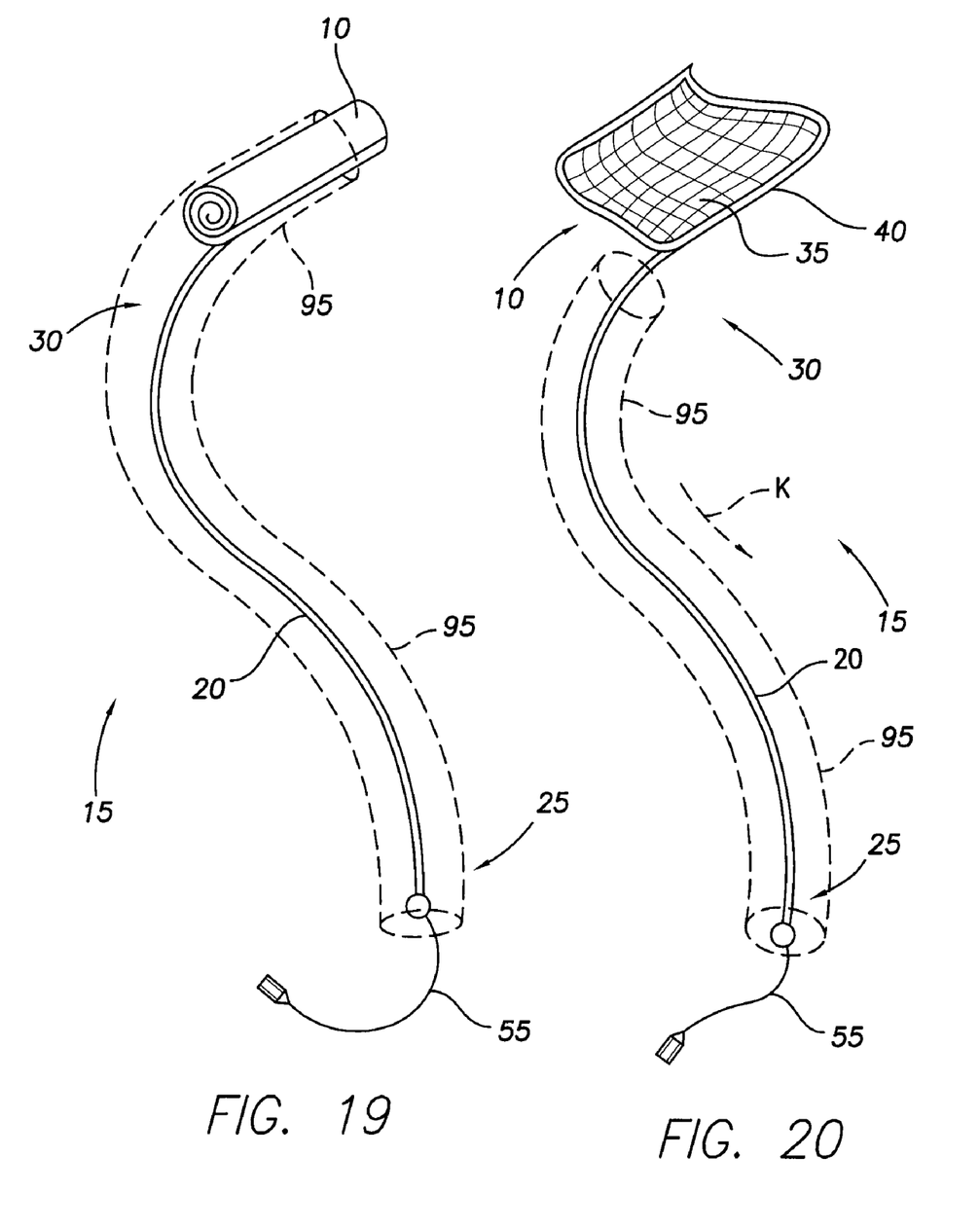
FIG. 19 is an overall view of the patch and lead, wherein the patch is in a non-deployed or unexpanded state.
FIG. 20 is the same view as FIG. 19, except the patch is in a deployed or expanded state.

In some embodiments, as shown in FIG. 12, the framework 40 is separate from the lead body 20 and is releasably or permanently attached to the distal end 30 of the lead body 20. In other embodiments, as depicted in FIGS. 14, 18 and 20, the distal end 30 of the lead body 20 forms the framework 40 by the distal end 30 coming about on itself to define the area across which the mesh 35 extends when in the patch 10 is in the deployed state. In other embodiments, as illustrated in FIG. 16, the distal end 30 of the lead body 20 forms the framework 40 by the distal end splitting into branches 40a, 40b, or otherwise defining the area across which the mesh 35 extends when the patch 10 is in the deployed state.

As illustrated in FIGS. 11, 13, 17 and 19, in various embodiments, when the patch 10 is in the non-deployed or unexpanded state, the patch 10 is folded, rolled or furled about itself along side the distal end 30 or a more proximal portion of the lead body 20. In other embodiments, when the patch 10 is in the non-deployed or unexpanded state, the patch 10 is folded, rolled or furled about the distal end 30 or a more proximal portion of the lead body 20. As depicted in FIG. 15, in various embodiments, when the patch 10 is in the non-deployed or unexpanded state, the patch 10 is folded, rolled or furled about itself at the distal end 30 or a more proximal portion of the lead body 20.

Figure 11:
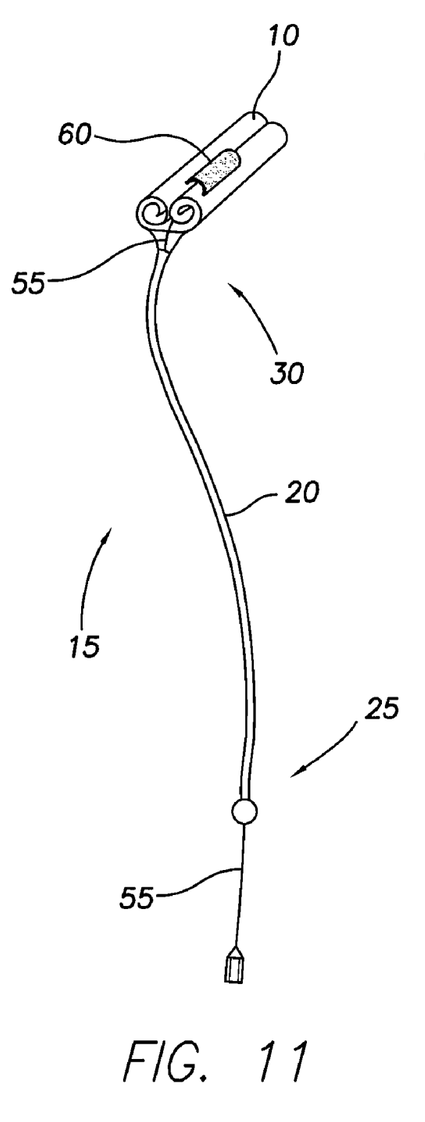
FIG. 11 is an overall view of the patch and lead, wherein the patch is in a non-deployed or unexpanded state.

As shown in FIG. 11, in one embodiment, the patch 10 is biased to deploy into the expanded state and includes Velcro-like mechanism 60 that maintains the patch 10 is a non-expanded state. A stylet or guidewire 55 or a drawstring 45 extends from the Velcro-like mechanism 60, through the lead body 20 and out the proximal end 25 of the lead body 20.

As depicted in FIG. 12, the patch 10 is deployed into the expanded or deployed state by pulling on the proximal end of the stylet or guidewire 55 or drawstring 45 (as indicated in by arrow G). As a result, the Velcro-like mechanism 60 is caused to release, which allows the patch 10 to unfold, unroll or unfurl into the deployed state.

As shown in FIG. 13, in one embodiment, the patch 10 is biased to deploy into the expanded state and includes an anchoring mechanism 50 (e.g., a pull-pin, latch, clip, barb, suture, etc.) that maintains the patch 10 is a non-expanded state. A stylet or guidewire 55 extends from an anchoring mechanism 50, through the lead body 20 and out the proximal end 25 of the lead body 20.

As depicted in FIG. 14, the patch 10 is deployed into the expanded or deployed state by pulling on the proximal end of the stylet or guidewire 45 (as indicated in by arrow H). As a result, the anchoring mechanism 50 is caused to release, which allows the patch 10 to unfold, unroll or unfurl into the deployed state.

As shown in FIG. 15, in one embodiment, the patch 10 is biased to deploy into the expanded state, but is maintained in a non-expanded state via an electroactive polymer that is electrically energized until the patch 10 is to be deployed. A first electrical conductor 65 extends from the electroactive polymer material of the patch 10, through the lead body 20 and out the proximal end 25 of the lead body 20 to a switch 70.

A second electrical conductor 75 extends from the switch 70 to a power source 80. An indifferent electrode 85 extends from the power source 80.

In one embodiment, the entire patch 10 is formed from an electroactive polymer material. In other embodiments, the mesh 35 or portions thereof are formed of an electroactive polymer material. In other embodiments, the framework 40 or portions thereof are formed of an electroactive polymer material.

As depicted in FIG. 15, when the switch 70 is closed to complete the electrical circuit and electrically energize the electroactive polymer material of the patch 10, the patch is maintained in the non-deployed or unexpanded state. As shown in FIG. 16, when the switch 70 is opened to break the electrical circuit, the electroactive polymer material relaxes, thereby allowing the bias of the patch 10 to cause the patch 10 to unfold, unroll or unfurl into the deployed or expanded state.

Figure 17:
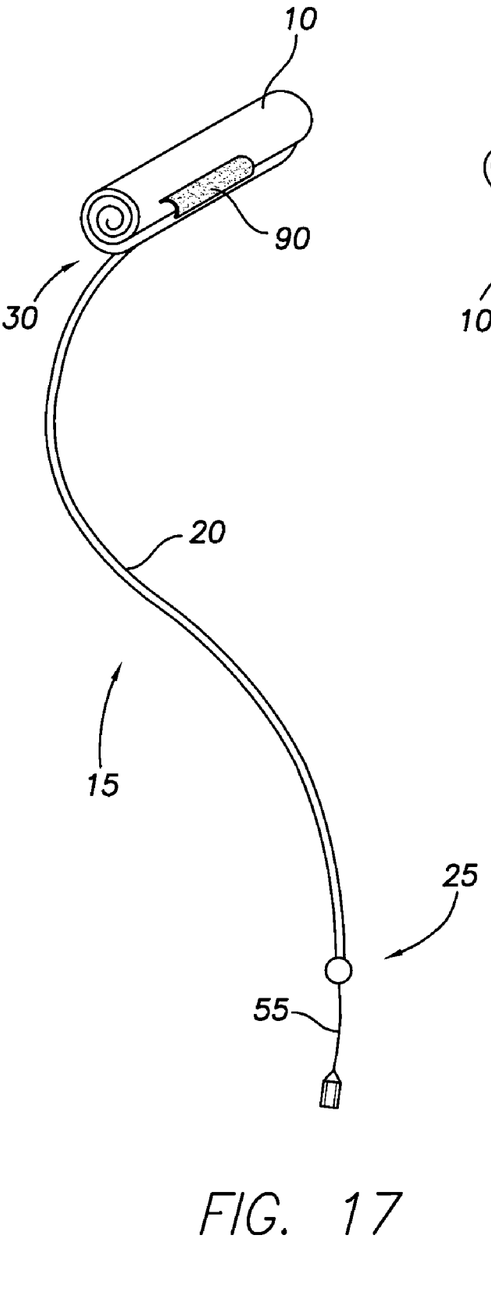
FIG. 17 is an overall view of the patch and lead, wherein the patch is in a non-deployed or unexpanded state.

As shown in FIG. 17, in one embodiment, the patch 10 is biased to deploy into the expanded state and includes an adhesive or bonding material 90 (e.g., Mannitol, fibrin based glues, cyano-acrylate glues, PEG based glues, glutaraldehyde-albumin cross linked glues, gelatin-resorcinol-formaldehyde ("GRF") glues, or any other biocompatible glue) that maintains the patch 10 is a non-expanded state. A stylet or guidewire 55 extends from the proximal end 25 of the lead body 20, through the lead body 20 to the junction between the lead body 20 and the framework 40 of the patch 10.

As depicted in FIG. 18, the patch 10 is deployed into the expanded or deployed state by extending the stylet or guidewire 55 distally (as indicated in by arrow J) such that the stylet or guidewire 55 extends into the framework 40 of the patch 10 to cause patch 10 to unroll, unfold or unfurl, thereby causing the adhesive 90 to fail and allowing the patch 10 to expand or deploy. It should be noted that a similar displacement of the stylet or guidewire 55 would also cause the Velcro-like material 60 of FIGS. 11 and 12 or the anchoring mechanism 50 of FIGS. 13 and 14 to release in a similar manner with the accompanying deployment of the patch 10.

As depicted in FIG. 18, in one embodiment, the adhesive 90 will dissolve after a few minutes within the patient. As a result, the adhesive 90 will release the patch 10, thereby allowing the patch 10 to unfold, unroll or unfurl into the deployed state.

As shown in FIG. 19, in one embodiment, the patch 10 is biased to deploy into the expanded state and the introducer sheath 95 (shown in phantom) maintains the patch 10 in a non-expanded state until the introducer sheath 95 is withdrawn proximally from the patch 10. As depicted in FIG. 20, the patch 10 is deployed into the expanded or deployed state by removing the introducer sheath 95 from about the patch 10. More specifically, the introducer sheath 95 is withdrawn proximally (as shown by arrow K) from the patch 10, which allows the patch 10 to unfold, unroll or unfurl into the deployed state.

To implant the patch 10, a lead 15 with a non-expanded patch 10 (see FIGS. 11, 13, 15, 17 and 19) located thereon is loaded distal end first into an introducer sheath. The lead 15, with the patch 10 located thereon, is advanced to the exterior surface of the heart via the introducer sheath 95. The introducer sheath 95 is withdrawn sufficiently to place the non-expanded patch 10 adjacent a myocardial infarction. Once properly positioned relative to the myocardial infarction, the patch 10 is deployed into the expanded state depicted in FIGS. 12, 14, 16, 18 and 20. Both prior to and after deployment, the patch 10 can be positioned via a stylet or guidewire 55 extending through the tubular lead body 20 to the patch 10.

Although the present invention has been described with reference to preferred embodiments, persons skilled in the art will recognize that changes may be made in form and detail without departing from the spirit and scope of the invention.

What is claimed is:

1. A pericardial lead comprising:
   an elongated lead body;
   a myocardial patch configured to be biased to normally assume an expanded state in the absence of a force acting against the bias; and
   an attachment mechanism having an unreleased state wherein at least a portion of the attachment mechanism is physically integrated with the patch so as to provide a force acting against the bias of the patch to thereby maintain the patch in its unexpanded state, and a released state wherein the attachment mechanism ceases to provide the force acting against the bias of the patch to thereby allow the patch to transition to its expanded state.

2. The lead of claim 1, wherein the patch includes a mesh extending between portions of a distal end of the lead body.

3. The lead of claim 2, wherein the distal end of the lead body is curved and the mesh extends between sides of the curve.

4. The lead of claim 2, wherein the distal end of the lead body branches into branches and the mesh extends between the branches.

5. The lead of claim 1 wherein the patch is releasably attached to the lead body.

6. The lead of claim 1 wherein the lead body comprises a lumen and the attachment mechanism comprises a drawstring extending through the lumen and having, in its unreleased state, a distal end of the drawstring attached to the patch so as to maintain the patch in a rolled, furled or folded unexpanded state.

7. The lead of claim 6 wherein the distal end of the drawstring is configured to separate from the patch upon application of sufficient tension force on the drawstring, to thereby transition the attachment mechanism to a released state and allow the patch to unroll, unfurl or unfold to its expanded state.

8. The lead of claim 6 wherein the distal end of the drawstring is woven into the patch.

9. The lead of claim 6 wherein the distal end of the drawstring is adhered to the patch.

10. The lead of claim 1 wherein the attachment mechanism comprises, in its unreleased state, an integral structure that attaches to a first portion and a second portion of the patch so as to maintain the patch in a rolled, furled or folded unexpanded state.

11. The lead of claim 10 wherein the lead body comprises a lumen and the pericardial lead further comprises a release mechanism sized to extend through the lumen so as to access the integral structure, wherein the integral structure in configured to interact with the release mechanism so as to separate to allow the patch to unroll, unfurl or unfold to its expanded state.

12. The lead of claim 11 wherein the integral structure comprises a contiguous piece of adhesive material configured to separate into at least two pieces upon interaction with the release mechanism.

13. The lead of claim 11 wherein, the integral structure comprises a first piece attached to the first portion of the patch and a second piece attached to the second portion of the patch and to the first piece, wherein the first and second pieces are configured to separate upon interaction with the release mechanism.

14. The lead of claim 13 wherein the first and second pieces comprise Velcro.

15. The lead of claim 11 wherein the integral structure comprises one of a pull pin, latch, clip, barb or suture configured to separate from one or both of the first and second portions of the patch upon interaction with the release mechanism.

16. The lead of claim 11 wherein the release mechanism comprises one of a drawstring, stylet or guidewire.

17. A myocardial patch for delivery via a pericardial lead having a lumen, the patch comprising:
   a framework including a lumen;
   a mesh extending between portions of the framework; and
   an attachment mechanism attached to one or both of the framework and mesh;
   wherein at least one of the framework and the mesh is configured to be biased to normally assume an expanded state in the absence of a force acting against the bias and the attachment mechanism has an unreleased state wherein at least a portion of the attachment mechanism is physically integrated with the patch so as to provide a force acting against the bias of the patch to thereby maintain the patch in an unexpanded state, and a released state wherein the attachment mechanism ceases to provide the force acting against the bias of the patch to thereby allow the patch to transition to an expanded state.

18. The patch of claim 17, wherein the framework is curved and the mesh extends between sides of the curved framework.

19. The patch of claim 17, wherein the framework branches into branches and the mesh extends between the branches.

20. The patch of claim 17, wherein the patch is rolled, furled or folded about itself or a portion of the lead.

* * * * *